US008870951B1

(12) United States Patent
Frazier et al.

(10) Patent No.: US 8,870,951 B1
(45) Date of Patent: *Oct. 28, 2014

(54) TOTAL ARTIFICIAL HEART SYSTEM FOR AUTO-REGULATING FLOW AND PRESSURE

(75) Inventors: Oscar H. Frazier, Houston, TX (US); William E. Cohn, Houston, TX (US)

(73) Assignee: Newheart Medical Devices LLC, Houston, TX (US)

( * ) Notice: Subject to any disclaimer, the term of this patent is extended or adjusted under 35 U.S.C. 154(b) by 200 days.

This patent is subject to a terminal disclaimer.

(21) Appl. No.: 13/467,468

(22) Filed: May 9, 2012

Related U.S. Application Data

(63) Continuation of application No. 12/485,015, filed on Jun. 15, 2009, now Pat. No. 8,226,712.

(60) Provisional application No. 61/061,530, filed on Jun. 13, 2008.

(51) Int. Cl.
*A61M 1/12* (2006.01)

(52) U.S. Cl.
USPC .......................................... 623/3.13

(58) Field of Classification Search
CPC ....................................... A61M 1/12
USPC ........................................ 623/3.13
See application file for complete search history.

(56) References Cited

U.S. PATENT DOCUMENTS

| 3,599,244 | A | 8/1971 | Wortman |
| 4,994,078 | A | 2/1991 | Jarvik |
| 6,080,182 | A | 6/2000 | Shaw |
| 6,342,072 | B1 | 1/2002 | Wartelle |
| 6,540,658 | B1 | 4/2003 | Fasciano |
| 6,855,291 | B2 | 2/2005 | Patterson |
| 7,172,727 | B2 | 2/2007 | Patterson |
| 7,238,165 | B2 | 7/2007 | Vincent |
| 7,588,530 | B2 | 9/2009 | Heilman |
| 7,704,054 | B2 | 4/2010 | Horvath |
| 8,210,829 | B2 * | 7/2012 | Horvath et al. ............... 417/350 |
| 8,226,712 | B1 * | 7/2012 | Frazier et al. ................ 623/3.13 |
| 2005/0107658 | A1 | 5/2005 | Brockway |
| 2008/0064917 | A1 | 3/2008 | Bar et al. |
| 2008/0306329 | A1 * | 12/2008 | Lu et al. .......................... 600/16 |
| 2010/0168848 | A1 * | 7/2010 | Horvath et al. ............. 623/3.13 |
| 2010/0292786 | A1 | 11/2010 | Tinker |
| 2011/0015732 | A1 | 1/2011 | Kanebako |
| 2011/0144744 | A1 | 6/2011 | Wampler |

FOREIGN PATENT DOCUMENTS

| WO | WO88/05313 | 7/1988 |
| WO | WO00/37139 | 6/2000 |
| WO | WO2007/044601 | 4/2007 |

OTHER PUBLICATIONS

English translation of WO88/05313, Jul. 28, 1988, Lapeyre.

* cited by examiner

*Primary Examiner* — Suzette J Gherbi
(74) *Attorney, Agent, or Firm* — Winstead PC

(57) ABSTRACT

The present invention is TAH system for auto-regulating blood flow and maintaining the asymmetric pressure balance in the mammalian cardiovascular system by decreasing the resistance in blood flow and minimizing the pressure gradients to exploit the in-flow pressure sensitivities of continuous flow pumps. The system further includes laminar flow generating manifolds connected to the atrium at one end and attached to pumps linked to the great vessels at the other, such that the in-let flow sensitivities of the pumps are maximized to auto-regulate blood flow, providing adequate pulmonary and systemic arterial flow to support normal metabolism and end-organ function and maintain the appropriate asymmetric physiologic pressure balance between the systemic and pulmonary systems of the mammalian cardiovascular system.

20 Claims, 8 Drawing Sheets

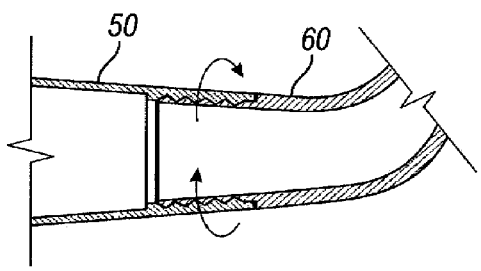
FIG. 6A
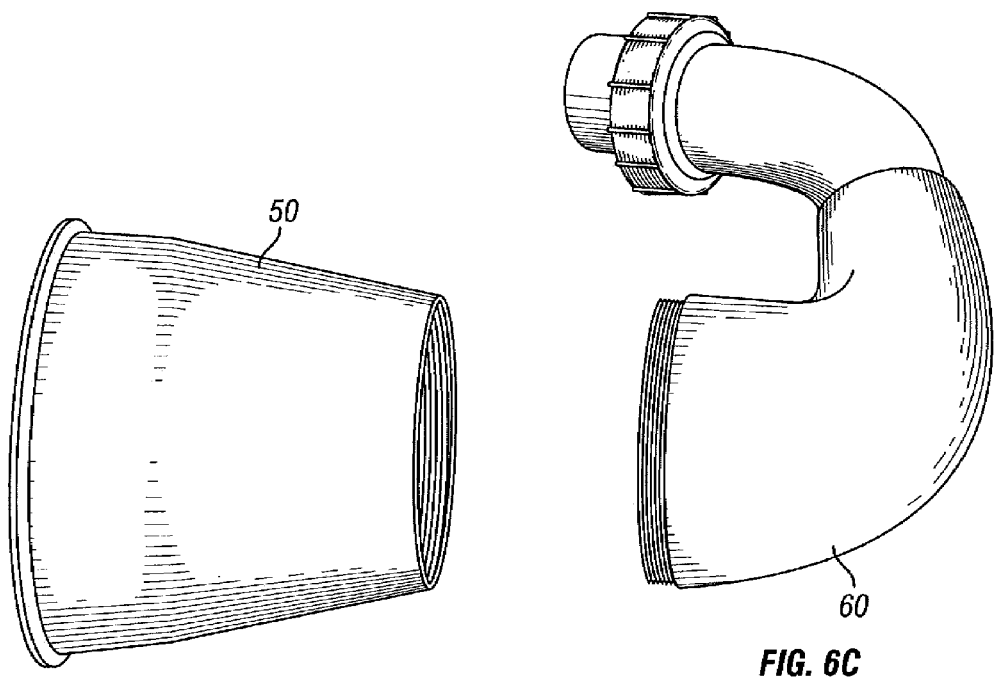
FIG. 6B
FIG. 6C

TOTAL ARTIFICIAL HEART SYSTEM FOR AUTO-REGULATING FLOW AND PRESSURE

CROSS-REFERENCE TO RELATED APPLICATIONS

This application is a continuation of U.S. patent application Ser. No. 12/485,015 filed Jun. 15, 2009 now U.S. Pat. No. 8,226,712, which claims priority to U.S. Provisional Patent Application 61/061,530 filed Jun. 13, 2008, each of which are incorporated by reference herein in their entirety.

BACKGROUND OF THE INVENTION

1. Field of Invention

The present invention relates to the field of cardiology and, more particularly, but not by way of limitation, to a total artificial heart (TAH) system and method for auto-regulating blood flow and appropriately maintaining the asymmetric physiologic balance between the systemic and pulmonary systems of the mammalian cardiovascular system.

2. History of Related Art

There are 3,500,000 people who have significant heart failure in the United States alone. Several hundred thousand people are diagnosed each year with congestive heart failure while another 50,000 die each year from this ailment. For most of these patients with heart failure, heart transplantation offers a reasonable option but severe limitation of donor organ availability limits its epidemiologic impact. Last year, approximately 2,000-2,100 heart transplants were performed in the United States and that number has been flat for the last several years.

Extra-corporeal ventricular assist devices providing mechanical circulatory support are routinely employed in patients with advanced heart failure in hospitals worldwide. Although for many patients, heart assist provides adequate palliation, there remains a large undeserved population in whom severe biventricular failure exists, and in whom mechanical circulatory support is inadequate. Additionally, prolonged use of the extra-corporeal ventricular assist devices can potentially lead to valve related complications. Hence, the development of a reliable completely implantable device to replace the heart could provide a valuable treatment option in these poorly served patients.

SUMMARY OF THE INVENTION

The present invention relates to cardiovascular systems but more particularly to a complete TAH system for auto-regulating blood flow and maintaining the asymmetric flow balance in a mammalian cardiovascular system. The TAH system disclosed herein achieves asymmetrical flow balance by decreasing the resistance to blood flow between the patient's pulmonary veins and the left pump and between the systemic veins and the right pump as well as minimizing pressure gradients in the continuously pumped blood between the systemic and pulmonary veins and the left and right pumps such that the changes in physiologic pressure systemic or pulmonary, are substantially transferred without a pressure gradient to the inlet of the continuous flow pumps where the pressure changes are exploited by the pump's innate ability to adjust for any physiologic variables. The system further includes connecting manifolds configured to maintain laminar blood flow from the residual left and right atrium at one end to the left and right respective pumps linked to the great vessels at the other. This configuration minimizes resistance to flow, decreases pressure gradients and allows the inflow pressure sensitivity of the pumps to be exploited to allow some degree of auto-regulation in maintaining the asymmetric flow balance between the systemic and pulmonary circulatory systems of the mammalian cardiovascular system.

Accordingly, one embodiment is a method for treating congestive heart failure and mimicking the functionality of the mammalian cardiovascular system by exploiting the in-flow pressure sensitivities of continuous flow pumps to allow auto-regulation of blood flow and maintain the appropriate asymmetric physiologic flow in the systemic and pulmonary systems of the mammalian cardiovascular system. The method further includes connecting manifolds onto a residual atrium at one end and attaching pumps linked to the great cardiac outflow vessels at the other end of the manifold. As blood flows from the body through the manifold to the continuous flow pumps set at a predetermined speed or RPM, changes in the blood pressure at the inflow are detected by the pumps which automatically respond accordingly and auto-regulate and in so doing, maintain the asymmetric balance in physiologic blood flow between the systemic and pulmonary circuits of the remaining mammalian cardiovascular system by either increasing or decreasing blood flow to counter balance the corresponding changes in inlet pressure. This response is due to the sensitivity of the continuous flow pumps to the pressure gradients across them created by the differences in the inlet and outlet pressures, such that an increase in atrial pressure on either pump will decrease the pressure gradient and result in an increase in pump output despite no change in pump RPM while conversely, a decrease in atrial pressure on either pump, will increase the pressure gradient resulting in a decrease in pump output.

Accordingly, another embodiment is a geometric configuration for laying out the components of a TAH such that the TAH is able to auto-regulate blood flow and maintain the asymmetric flow balance in the mammalian cardiovascular system by exploiting the in-flow pressure sensitivities of continuous flow pumps, is disclosed. The geometric configuration includes laying out and orienting a manifold, pump and graft such that the laminar blood flow generated allows the inlet sensitivity of the pump to exploit the pressure changes, and as such, auto-regulate and maintain the asymmetric pressure balance between the systemic and pulmonary circulatory systems of the mammalian cardiovascular system.

The technical advantages of certain embodiments of the invention include being compact enough to fit within the mediastinum of an average-sized patient but robust enough to address the cardiac output requirements of large patients. Additionally, the embodiments eliminate inefficiencies by being self-contained and allow patients to be un-tethered, ambulatory, and able to resume normal or near-normal activity. The embodiments can pump continuously for 5 or more years without maintenance and do not injure the formed elements of blood or create thrombi or emboli. Furthermore, failures when they occur, are predictable "soft" failures that allow for simple pump replacement or transplantation, if indicated. Most important, the embodiments provide adequate pulmonary and systemic arterial flow to support normal metabolism and end-organ function and maintain the appropriate physiologic balance between the systemic and pulmonary systems of the mammalian cardiovascular system. Particular embodiments may include one, some, or none of the listed advantages.

The foregoing has outlined some of the features and technical advantages of the present invention in order that the detailed description of the invention that follows may be better understood. Additional features and advantages of the invention will be described herein after which form the subject of the claims of the invention.

BRIEF DESCRIPTION OF THE DRAWINGS

A more complete understanding of the system of the present invention may be obtained by reference to the following Detailed Description when taken in conjunction with the accompanying Drawings wherein:

FIGS. 6a-6c are side views of a manifold used in generating laminar flow and reducing pressure resistance within this manifold itself as well as its component parts; in accordance with an embodiment of the present invention;

FIG. 6a is a side view of the top conical section and the lower U-shaped section snuggly fitted together but with an allowance such that the components can be rotated around this fitting to allow the TAH to fit into the chest cavity; in accordance with an embodiment of the present invention;

FIG. 6b is a view of the top conical section which along with the lower U-shaped section form the curved funnel shaped compliance chamber; in accordance with an embodiment of the present invention;

FIG. 6c is a view of the lower U-shaped section which along with the top conical section form the curved funnel shaped compliance chamber; in accordance with an embodiment of the present invention;

NOTATION AND NOMENCLATURE

Figure 1:
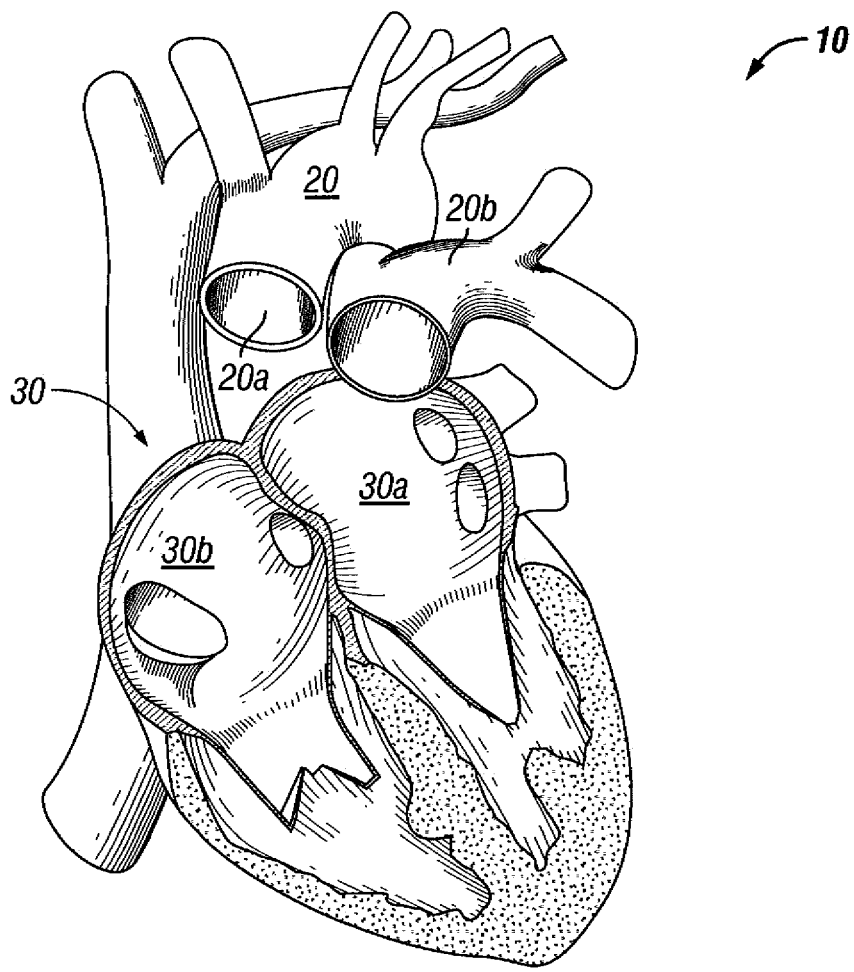
FIG. 1 illustrates an inside view of a cross-section of the cut-off ends of the aorta, pulmonary artery, and the residual right and left atria prior to implantation of the TAH in accordance with an embodiment of the present invention.

Certain terms are used throughout the following description and claims to refer to particular system components. This document does not intend to distinguish between components that differ in name but not function. In the following discussion and in the claims, the terms "including" and "comprising" are used in an open-ended fashion, and thus should be interpreted to mean "including, but not limited to";

The term "asymmetric balance" refers to the physiological necessity of the mammalian cardiovascular system in which the pulmonary circuit flow and the systemic circuit flow have different values but remain substantially constant and proportional, within a healthy physiological range. In this term, however, is the reality that the two are not equal. However, they must meet and remain in an appropriate physiologic balance, systemic flow being slightly higher than the pulmonary flow due to the bronchial circulation which arises from the left and returns to left;

The term "auto-regulate" refers to the innate ability of the continuous flow pumps to respond to changes in their inflow pressure by increasing or decreasing blood flow without the need for external sensors or controllers;

The term "continuous flow pump" is used to describe any pump that uses a rotating member that spins at a constant RPM to generate flow. This includes pumps that may be adjusted to simulate a pulse;

The term "dysrhythmia" refers to an irregular heart rhythm or wave;

The term "edema" refers to excess accumulation of fluid or blood in the tissues;

The term "embolus" refers to an object(s) or foreign entities/objects(s) not normally found in the blood such as a blood clot that causes blockage of the blood vessels;

The term "hemolysis" refers to the destruction or dissolution of red blood cells;

The term "laminar flow" refers to normal condition for blood flow throughout most of the circulation system.

The term "mediastinum" refers to the area between the lungs;

The term "reversible physiological stress event or physiologic perturbations" refers to any temporal physiological change such as coughing, changing posture, and evacuating bowels, amongst other activities or events that can affect vascular resistance or volume status, blood flow and blood pressure;

The term "stasis" refers to the slow or reduced blood movement which could lead to blood clots or other harmful effects;

The term "blood flow shearing" refers to the interaction of a fast blood flow with a relatively slower blood flow which may lead to harmful platelet aggregation, red blood cell damage and other harmful effects;

The term "thrombi" refers to blood clots formed within the vessels but not dislodged from their point of origin;

The term "thromboembolism" refers to the blocking of blood vessels by blood clots dislodged from their point of origin; and The term "total artificial heart" (TAH) is used to describe any system, including any combination of synthetic and biological components, designed to be implanted in the body and to replace the natural pumping functions of the human heart.

In addition to the standard definition, the term atria or atrium may also refer to the residual or remnant atria or atrium present following surgical removal of the natural atria or atrium of the diseased heart prior to transplant of the TAH of the present invention.

DETAILED DESCRIPTION OF THE INVENTION

In the following detailed description, reference is made to the accompanying drawings that show, by way of illustration, specific embodiments in which the invention may be practiced. These embodiments are described in sufficient detail to enable those skilled in the art to practice the invention. It is understood that the various embodiments of the invention, although different, are not mutually exclusive. For example, a particular, feature, structure, or characteristic described herein in connection with one embodiment may be implemented within other embodiments without departing from the spirit and scope of the invention. In addition, it is understood that the location or arrangement of individual elements within each disclosed embodiment may be modified without departing from the spirit and scope of the invention. The following detailed description is, therefore, not to be taken in a limiting sense, and the scope of the present invention is defined only by the appended claims, appropriately interpreted, along with a full range of equivalents to which the claims are entitled. In the drawings, like numerals refer to the same or similar functionality throughout the several views.

Although significant progress in the development of a total artificial heart has been made over the past forty years, improvements in durability and thrombo-embolic performance and reduction in size are desperately needed. The externally actuated pneumatic heart, first developed by Liotta and DeBakey, and subsequently refined by Jarvik, has continued to evolve since it was first implanted in man by Cooley in 1971. The CardioWest Artificial Heart, arguably the most evolved form of this technology, has been implanted in patients worldwide. However, the device has limited durability which has restricted its use to short and intermediate term support of patients awaiting cardiac transplantation. Furthermore, the means of actuation of the CardioWest heart necessitates that the patient remain tethered by pneumatic tubes to a drive console, which severely limits their ability to return to an active lifestyle. The AbioCor device; is currently the most advanced completely self-contained total artificial heart and was first implanted in 1996. However, this device suffers from mechanistic complexity resulting in limited durability. Additionally, the AbioCor device is quite large which limits implantation to patients with a body surface area of two square meters or greater, which includes only the largest quartile of patients suffering from heart failure.

Hence, a significant departure from previous artificial heart design efforts is required if the size and durability issues are to be successfully overcome. A continuous flow TAH that capitalizes on the improved durability and decreased size of axial flow and centripetal flow pumps may provide one possible solution. Axial flow and centripetal flow pumps, in contrast to traditional volume displacement pumps have a single rapidly spinning rotor or impeller that imparts hydraulic energy to the blood, resulting in continuous flow, like that produced by a water faucet. This mechanism obviates the need for valves and flexible membranes. The mechanical simplicity of the continuous flow pumps makes these significantly smaller, more energy efficient, and much less susceptible to mechanical wear. These characteristics make them well suited for integration into a completely implantable TAH.

Independent of the concession that a total artificial heart (TAH) may prove valuable in patients with severe biventricular failure, there are some other reasons why total cardiac replacement may be advantageous when compared to implementation of mechanical cardiac assist in a broader group. Experience over the last two decades have shown compellingly that a mechanical pump can augment the performance of a weak left ventricle, and in many cases, supplant function altogether. However, prolonged left ventricular support can result in damage to the native aortic valve. In the unassisted heart, the aortic valve is only required to maintain competence against systemic diastolic pressure. In contrast, after Left Ventricular Assist Device (LVAD) implantation, the closed valve is exposed to systolic pressure, which after prolonged periods can result in leaflet fusion and valvular insufficiency. This insufficiency can result in a decrease in LVAD efficiency and/or hemolysis, both of which can impact outcome.

Similarly, in patients with severely compromised left ventricles, systolic opening of the native aortic valve may become intermittent, or stop altogether, even at low levels of mechanical support. This stasis resulting from convergent flow paths can result in thrombus formation above the aortic valve, especially adjacent to the non-coronary leaflet, which can lead to catastrophic thromboembolism. This can be especially problematic if the pump outlet is attached too high on the ascending aorta, or if a distal site for outflow graft attachment such as the descending thoracic aorta has been utilized. Similarly, patients in whom a prosthetic aortic or mitral valve has been previously implanted are at increased risk of developing stasis and thrombotic prosthetic valve complications in this setting. Removing all native heart valves, as is done with TAH implantation, avoids these potential valve related complications.

Interference of internal cardiac structures with LVAD or Right Ventricular Assist Device (RVAD) inflow cannula function can prove challenging. Although the sintered Titanium surface of the inflow cannula used in the HeartMate XVE and HeartMate II devices generally forms a smooth neointima and does not seem to be a source of thrombus generation, thrombus formation around the base of other non-textured inflow cannulas in a variety of devices has been observed. Furthermore, the ventricular septum, lateral left ventricular wall, and portions of the subvalvular apparatus of the mitral valve may interfere with the inflow cannula, impeding flow or causing hemolysis or problematic ventricular dysrhythmia. Lastly, the left atrial appendage in the fibrillating heart poses a significant risk of thromboembolism in many patients. Although judicious anticoagulation may mitigate many of these risks, intracranial and gastrointestinal hemorrhage is occasionally seen in patients chronically supported with implantable LVADs, which complicates management of anticoagulation. A TAH design that avoids convergent and divergent flow paths, simplifies the interface between the patient and the device, and minimizes areas of stasis may be less problematic from these perspectives.

Recently, there has been a trend towards the use of implantable assist devices for destination therapy, as a permanent end-state device to chronically support the failing heart of patients who are not candidates for transplantation. Most patients with end-stage heart failure have significant cardiac enlargement and as such, space in the chest is limited. Implanting two separate assist pumps in a manner that results in acceptable pump orientation, unobstructed inlet cannula position, and non-kinking lay of both outflow grafts may prove challenging. This challenge will be exacerbated in small patients, and in patients with right ventricular geometry that complicates obtaining an unobstructed inlet. In these patients removing the heart and replacing it with a TAH may be technically simpler. Moreover, removing the enlarged heart will in all likelihood provide adequate space in which a TAH can be positioned in many patients.

For the aforementioned reasons, there is a need in the art for a simple auto-regulating, asymmetric balancing TAH system with an automaticity factor such that as the filling pressure of either pump starts to change, it automatically responds by auto-regulating the flow and restoring the asymmetric pressure balance between the left and right mammalian cardiovascular systems. Additionally, the TAH should be compact enough to fit within the mediastinum of an average-sized patient while robust enough to address the cardiac output requirements of large patients. Furthermore, the TAH should be self-contained and allow patients to be un-tethered, ambulatory, and able to resume normal or near-normal activity. The TAH should also be able to pump continuously for 5 or more years without maintenance and not injure the formed elements of blood or create thrombi or emboli. Like in all devices, failures when they occur, should be predictable "soft" failures that allow for simple pump replacement or transplantation, if indicated. Most important, the TAH should provide adequate pulmonary and systemic arterial flow to support normal metabolism and end-organ function and be able to maintain the appropriate asymmetric physiologic balance between the systemic and pulmonary systems. The continuous flow TAH, as described herein, is uniquely suited to achieve these objectives.

FIG. 1 shows a cross-section of the heart 10 after sections have been surgically removed prior to a transplant. With the ventricles and much of the atria removed, the cut-ends of the thinner walled pulmonary artery 20b, the aorta 20a, the residual right atrium 30b, and the residual left atrium 30a are exposed, and ready for attaching a TAH system 100 that can pump blood from the right atria remnant 30b to pulmonary artery 20b and from left atria remnant 30a to aorta 20, fit in the chest, and auto-regulate and maintain the asymmetric balance in pressure between the systemic and pulmonary systems of the mammalian cardiovascular system.

Figure 2:
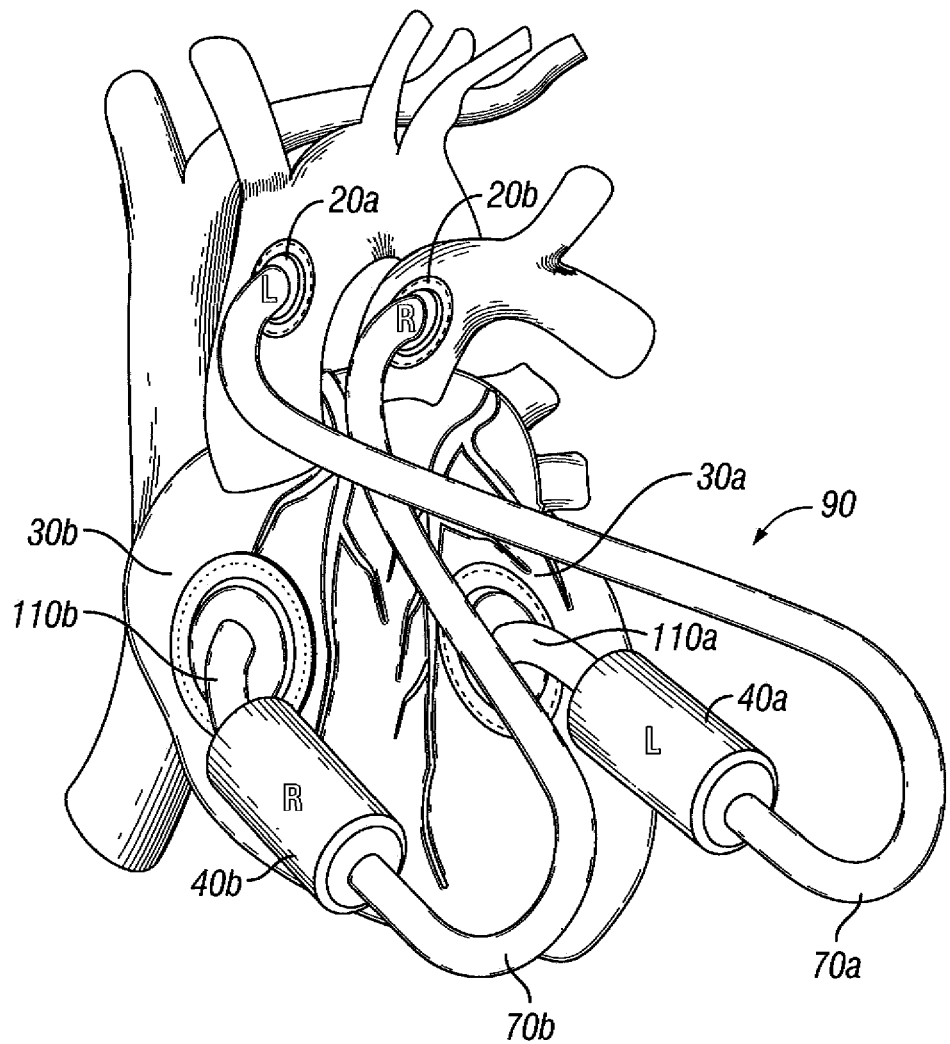
FIG. 2 illustrates a view of the TAH, with the pumps attached closer to the heart tissue on the descending limbs of the U-shapes formed by long grafts extending from the pumps to the great vessels in accordance with the simplest embodiment of the present invention.

FIG. 2 shows a configuration of the TAH system 90 in accordance with one embodiment of the present invention. The TAH system 90 comprises a right inflow graft 110b, a left inflow graft 110a, a right pump 40b, a left pump 40a, a right out-flow graft 70b and a left outflow graft 70a. The pumps 40 are micro axial-continuous flow pumps that can fit in the chest. The inflow grafts 110 and the outflow grafts 70 are natural or synthetic material, including both inelastic and elastic materials, having sufficient flexibility, resiliency and pliability to enable them to twist and fold as in the outflow grafts 70, to form two crossing interconnecting U-shaped sections, connecting the great cardiac outflow vessels 20 to the pumps 40 and then to the inflow grafts 110 during the TAH system's 90 circulation of blood from the right atrium 30b to pulmonary artery 20b and from left atrium 30a to aorta 20a.

Figure 3:
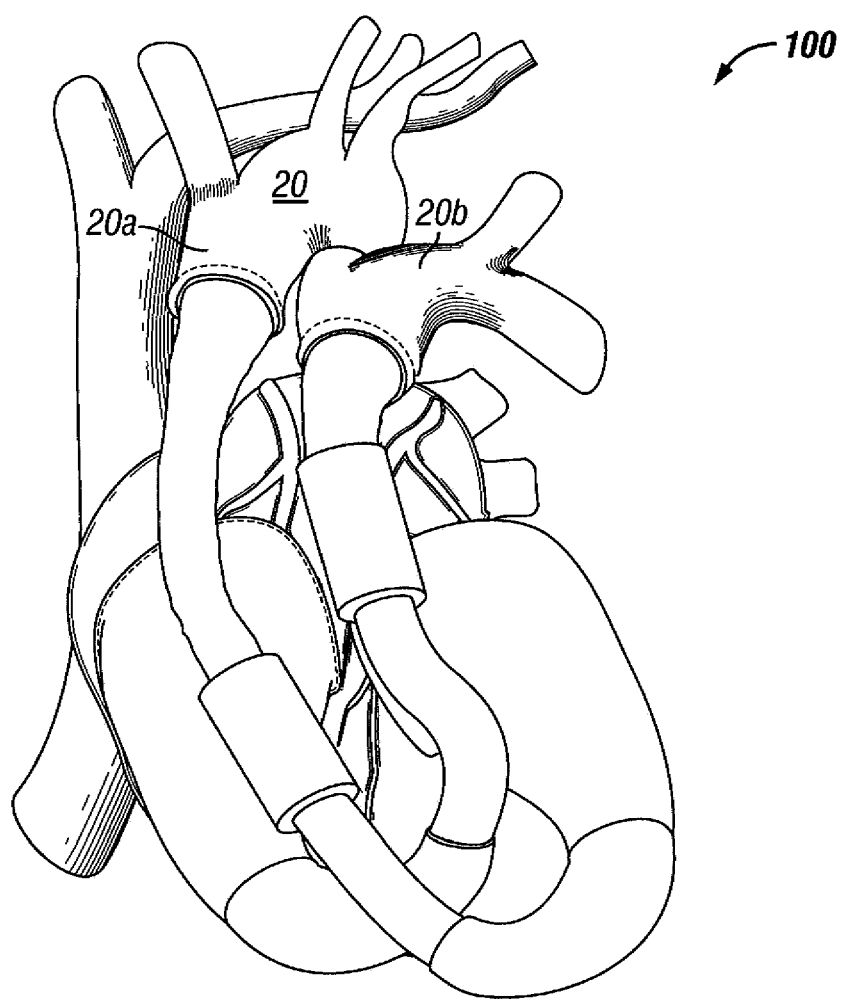
FIG. 3 illustrates a view of the TAH with short grafts extending from the pumps to the great vessels and the pumps attached further from the heart tissue on the ascending limbs of the U-shapes formed by curved manifolds which allow a large compliance chamber to be added to the residual atria minimizing the impact of reversible physiological stress events or perturbations in accordance with an embodiment of the present invention.

FIG. 3 shows an embodiment of a TAH system 100 of the present invention. The TAH system 100 comprises of, a right pump 40b, a left pump 40a, a right out-flow graft 70b, a left outflow graft 70a and a right manifold 120b and left manifold 120a, each comprising of top conical section 50 and lower U-shaped section 60 to form a funnel shaped curved reservoir through which the blood flows from the residual atrium 30 to the pump 40.

During circulation in any TAH system utilizing two continuous flow pumps, the demands on the two pumps are different given that there is an asymmetric balance that needs to be maintained in the mammalian cardiovascular system between pulmonary flow and the systemic flow. More subtly, this complexity arises because the structure and physiology of mammalian cardiovascular system is such that the left ventricle and right ventricle pump different amounts of blood or different volumetric amounts per unit time. As such, all the blood that the right heart ejects is pumped out through the pulmonary artery to the lungs and back to the left side of the heart. As for the left side of the heart, some of the blood it ejects goes out the aorta through small bronchial vessels that supply the bronchus and a small bit of the lung architecture, and back through the pulmonary veins into the left side of the heart. Because of all the blood from the right flowing to the left and only a majority of the blood from the left flowing to the aorta, with the rest short circuited back to the left side of the heart, there is a natural imbalance in flow between the left and right sections of the mammalian cardiovascular system. While the natural disposition of the mammalian cardiovascular system is to function with this asymmetric balance to deliver oxygenated blood to the whole body at inordinately low filling pressures and with flow rates consistent with being alive and functioning, accounting for this disparity is a challenge for current artificial hearts.

In humans, the excess blood circulating back may be only a couple cubic centimeters per heartbeat but if allowed to add up over the course of a day, the cumulative effect could result in death. If for example, in a conventional artificial heart system where the physiology of the patient results in a setting of the right and left pumps such that the right pump is hypo functioning, then the filling pressure of that right side would gradually increase such that the pump will malfunction and not meet its physiological demands or output requirements. With this continuing increase in filling pressure, eventually the liver and kidneys will fail and the patient will die. Conversely, a cumulative effect over every heartbeat would also occur if the two pumps are unbalanced because the left pump is hypo functioning relative to the right. As the filling pressures of the left heart or the pulmonary venous pressure gradually increase over time, the lungs will get more and more saturated with blood, resulting in a pulmonary edema and death. Similar consequences will arise if one of the pump stops working and becomes a passive conduit at high enough in-flow pressure. Conventional attempts at overcoming this problem have utilized electronic monitoring and control devices for changing the pump speed. However, any solutions involving electronic control systems are generally unsuitable for long term patient survival due to the inherent limitations on the reliability and longevity of electronic sensors and control systems. The presently disclosed TAH continuous flow system auto-regulates and asymmetrically balances pressure without the help of electronic control systems and provides a compact TAH system and configuration that integrates and balances the flow rate with in-flow pressure sensitivity.

The example artificial heart system in FIG. 3, is a robust auto-regulating, asymmetric balancing TAH system with an automaticity factor such that, as the filling pressure of either pump starts to gradually increase or decrease, the system automatically responds by auto-regulating the flow and restoring the asymmetric physiological balance between the left and right mammalian cardiovascular systems. The shape and configuration of the manifolds 120, the pumps 40 and the outflow grafts 70 is designed to auto-regulate and maintain the asymmetric balance. In an exemplary embodiment, the manifold comprises of a top conical section 50 and a lower U-shaped section 60 such that the diameter of the manifold gradually and smoothly tapers from about 5 inches to about 1 inch just before the pump 40 inlet forming a compliance chamber or reservoir. This gradual and smooth decrease in the cross-sectional diameter of the conical section 50 and the U-shaped section 60, ensures minimal resistance to flow rates and creates a velocity profile such that the blood flow is substantially laminar Additionally, this geometry and shape of the manifold 120 as it slowly tapers down and then curves slightly toward the end of the U-shaped section facilitates this laminar flow of blood and ensures that there is no blood flow shearing or stasis.

The shape also allows the TAH system 100 to be positioned within the chest cavity in a compact fashion. With the blood flowing through the manifold unimpeded, the change in the pressure between the section of the manifold 120 in contact with the residual atrium 30 and the inlet of the pump 40 is minimized Ideally, the change in the pressure should be about zero but this TAH system 100 can function with pressure differentials of up to about five or six millimeters while still allowing the inlet of the pump 40 to detect the actual physiological pressure. The configuration, shape and alignment of the manifold 120, therefore allows the pumps 40 to have a substantially direct and unobstructed sense of the pressure changes, thereby allowing the spinning elements in the pumps 40 to detect the differences in inlet pressure and exploit pressure sensitivity differences to automatically auto-regulate flow and asymmetrically balance the pressure in the mammalian cardiovascular system while pumping blood from the right atrium 30b to pulmonary artery 20b and from left atrium 30a to aorta 20a.

This dual synchronized operation of each half of the TAH 100 is critical because each pump 40 acts as an input in providing blood to the other. For example, during circulation, one pump 40, pumps blood to the lungs which then flows to the second pump 40 and is then pumped through the aorta to the whole body, eventually flowing back to the first pump 40. With the pumps 40 thus working together, the TAH system 100 allows each of the pumps 40 to immediately detect and respond to pressure changes in the circulatory system due to circumstances such as acute reversible physiological stress events, by either increasing or decreasing the flow of blood and maintaining the asymmetric physiologic balance between the left and right sides of the mammalian cardiovascular system. The TAH 100 system also allows automatic auto-regulation and asymmetric pressure balancing without the need for electronic or external devices. Furthermore, unlike conventional artificial heart systems, the TAH system 100 is more efficient as it is connected directly to the atrial remnant of the subject, auto-regulating and balancing the asymmetric pressure by attenuating the pressure drops between the atrial remnant 30 and the inlet of the pump 40. An exemplary manifold 120 shape is illustrated in FIG. 3. Other shapes that provide the desired characteristics are also contemplated.

The TAH system 100 was used in animal studies, with the TAH specifically adapted for animal studies, the objective being to completely excise the hearts of male Corrente-X calves (70-80 Kg) and replace them with two continuous flow pumps, one providing systemic circulation and the other providing pulmonary circulation. Under general endotracheal anesthesia, a left thoracotomy was performed and the animals were cannulated and placed on normothermic cardiopulmonary bypass (CPB). The arterial cannula was inserted in the left carotid artery. Dual venous cannulation was performed using the left jugular vein and the junction of the right atrium and inferior vena cava. After institution of total CPB, the ascending aorta was cross-clamped and the heart was excised. Generous left and right atrial remnants were preserved, but both atrial appendages were excised. The aorta and pulmonary arteries were transected above their respective valves. With heart of a cow cut out exposing the cut-ends of the thinner walled pulmonary artery 20b, the aorta 20a, the right atrial remnant 30b, and the left atrial remnant 30a the TAH system 100 could be now be implanted to restore the cardiovascular functions usually performed by the heart. First, the top conical sections 50 of the manifold 120 were connected to the atrial remnants. Next the U-shaped lower sections 60 of the manifold were attached to closely fit the bottom section of the conical section 50 and rotated into appropriate position forming a curved funnel shape gently tapering down manifold 120 for laminar blood flow. With the manifolds 120 in position, the pumps 40 were screwed on to them and outflow grafts 70 attached at the opposite end of the pump 40. The short outflow grafts 70 were then sown unto the great cardiac outflow vessels 20 forming a conduit for pumping blood from the right atrial remnant 30b to pulmonary artery 20b and from left atrial remnant 30a to aorta 20a as in a normal circulatory system. The bypass system was then taken off and blood introduced through the atrium 20 into the slowly tapering manifold 120. With the shape and nature of the manifold 120, offering nominal resistance, blood flow was generated by a velocity profile that allowed blood to flow at a faster down the middle and at a slower rate down the sides. With no blood flow shearing or stasis, and only continuous laminar flow of blood, the changes in pressure at the section of the manifold 120 in contact with the atrial remnant 30 were substantially transferred to the inlets of the pumps 40. This efficient transfer of the pressure at the points of contact to the inlets of the pumps 40, allowed the pumps' 40 spinning elements to exploit their sensitivity capabilities to inlet pressure changes by immediately transmitting this pressure changes across the pump 40 and minimizing the pressure gradient between the inflows and outflows of the manifold 120. With minimal or nominal pressure differentials between these inflows and outflows, the TAH was able to more accurately and immediately detect pressure changes in the circulatory system and adjust for them through auto-regulation and asymmetric pressure balancing by increasing or decreasing the rate of blood flow. After the surgery was complete the cow was able to exercise on the treadmill without difficulty.

Still referring to FIG. 3, the TAH system 100 is oriented and streamlined to allow the conical section 50 of the manifold 120, the U-shaped section 60 of the manifold 120, the outflow grafts 70 and the pumps 40 to fit in the allotted space in the chest and maintain the natural orientation of blood flow. Unlike the TAH system 90 in FIG. 2, where the orientation is such that the outflow grafts 70 increase the resistance to blood flow by twisting and folding to form two crossing interconnecting U-shaped sections, the TAH system 100 in FIG. 3 is compact such that it can easily be fitted into the chest as the grafts to do not overlap while connecting to the great cardiac outflow vessels 20.

For a human, the manifold 120 may have an approximate length of 2 to 10 inches. The manifold 120 atrial cuff (where the manifold 120 connects to the atrium 30) has an approximate diameter of 3 to 5 inches. The manifold 120 tapers down to a diameter of approximately 0.5 inch to 1.5 inches. The manifold 120 has an approximate volume of 30 to 500 cubic centimeters. The curvature of the manifold 120 varies from about 150 to 210 degrees. These preceding ranges are for an average adult human. These values may vary based on age, gender, body mass and other similar factors.

Still referring to FIG. 3, the outflow grafts 70 may be made of natural or synthetic material, including both inelastic and elastic materials, having sufficient flexibility, resiliency and pliability to enable them to twist and fold. The out-flow grafts may be short e.g., about 4 inches as this will offer little or no resistance. The exterior of the manifold 120 may be made of reinforced material to ensure that it holds the right geometry while internally it is made of suitable blood contacting material. The top conical section 50 may be made from fiber or silicon like material such that cut into different lengths depending on the size and age of the patient while the bottom U-shaped structure 60 may be supported with titanium like material or externally supported to ensure that it is not collapsible. The dimensions of the bottom half of the conical section 50 may be configured to tightly or snuggly fit inside the upper section of the U-shaped section 60 yet allowing room for the lower U-shaped section 60 to rotate or swivel into the appropriate position during surgery. These components could be made from the materials including but not limited to plastics, GOR-TEX® and Dacron.

Still referring to FIG. 3, this TAH system 100 comprises the replacement of the excised heart with two continuous flow pumps 40, where the inflow pressures remain largely stable and the resultant circulation is truly pulseless. In a continuous flow system, blood is continuously pumped through the body rather than pulsing the blood rhythmically as in the human heart. In the past, TAHs have been based on a pulsatile system in an effort to mimic normal mammalian physiology but in recent years, research has focused on continuous flow systems. Although to date over 1,200 patients have been implanted with continuous flow pumps as ventricular assist devices, generally these patients maintain pulsatile circulation. This is because the flow produced by a continuous flow pump is very sensitive to the pressure difference between the pump outflow and inflow cannulas. As this pressure gradient decreases, pump output increases. During ventricular systole, the pressure at the pump inflow rises briskly, thereby decreasing the gradient. This results in an increase in pump flow during systole, despite constant rotor speed. This cyclic increase in instantaneous pump flow results in generation of a pulse, albeit with a decreased amplitude, even if the aortic valve remains closed throughout the cardiac cycle. If, however, as in the current TAH 100, the heart is excised and replaced with two continuous flow pumps, inflow pressures remain stable, resulting in a truly pulseless circulatory system. The revolutions per minute (RPMs) of the continuous flow pumps can, however be quickly altered to generate a big burst of flow and create a pulse effect, in the event of a need for operating this TAH system 100 in a pulsating mode. The asymmetric balancing is achieved by running similar or different pumps 40 at different established speeds (RPMs) to maximize the in-flow pressure sensitivity of the pumps. A centrifugal pump 80 (FIG. 8) can be substituted for the axial continuous flow pump 40. Centrifugal pumps are sensitive to in-flow and out-flow pressures, resulting in better auto-regulation and asymmetrical pressure balancing, and their shape allows for a tangential out-flow which makes them easier to fit into the chest. The RPMs of the pumps 40 can also be monitored or programmed remotely, to provide adjustments in the operation of TAH system 100 e.g. wireless monitoring or programming.

Figure 4:
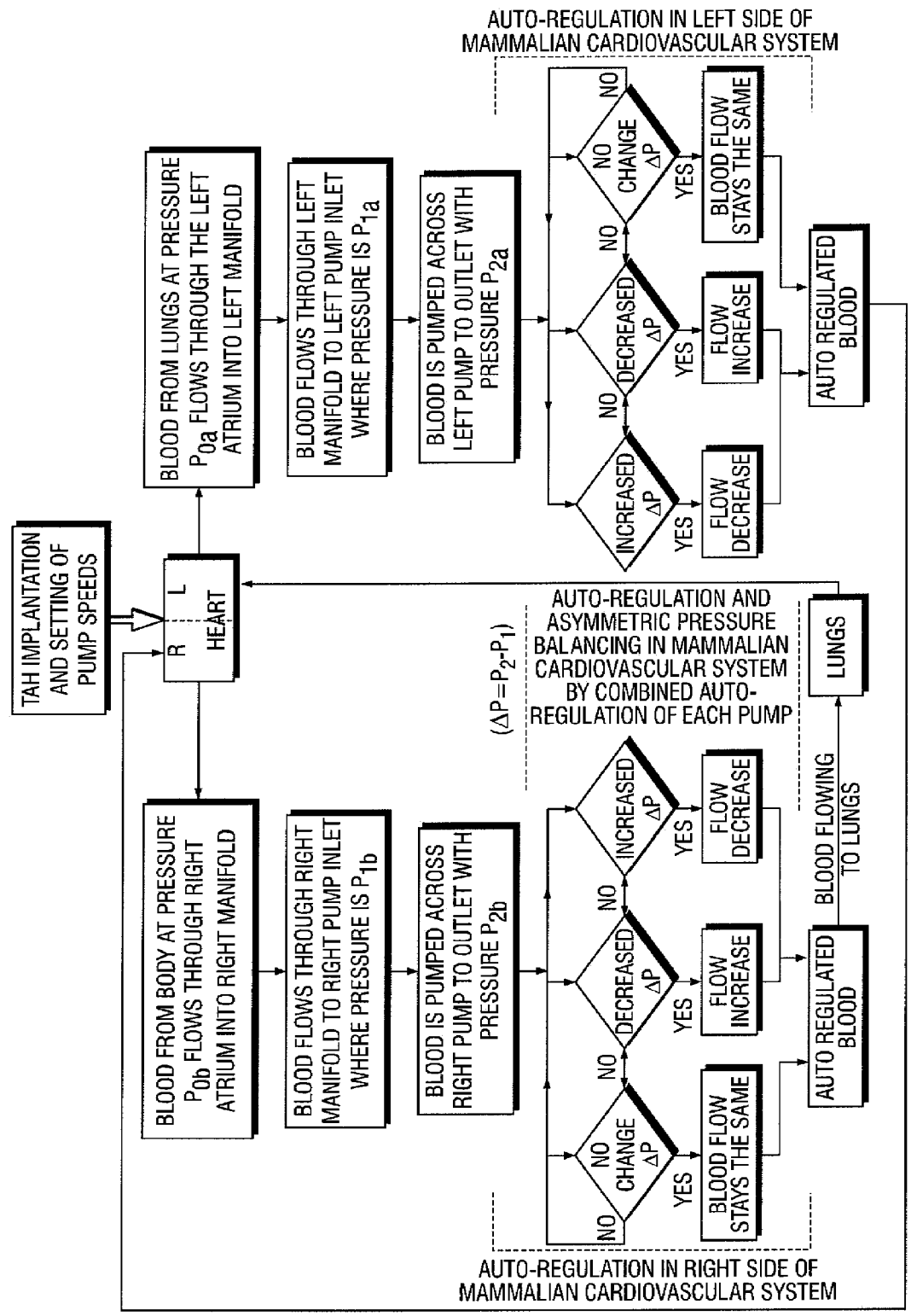
FIG. 4 is a schematic illustration of the TAH system as it auto-regulates and asymmetrically balances for changes in inlet and/or outlet pressure by increasing or decreasing blood flow when implanted in a mammalian cardiovascular system.

FIG. 4, is a schematic illustration of the TAH system 100 when implanted in a mammalian cardiovascular system. After the TAH system 100 is connected to the remnants of the heart and the bypass system is removed, deoxygenated blood from the body at a pressure $P_{0b}$ is allowed to flow into the residual right atrium 30b and then into the right manifold 120b. Due to its shape and configuration, the right manifold 120b offers nominal resistance and allows continuous laminar blood flow to the inlet of the right pump 40b such that $P_{0b}$ is substantially the same as $P_{1b}$. The blood is then pumped across the right pump 40b, generating outflows with pressure $P_{2b}$. For a mammalian circulation system, the outflow pressure at the outlet of the pump $P_2$ is always substantially greater than the inflow pressure $P_1$ for every condition and physiologic state. If during the circulation cycle, the body's pressure $P_{0b}$ remains substantially unchanged and hence the inlet pressure $P_{1b}$ stays substantially the same such that the change in pressure $\Delta P (P_2-P_1)$ stays substantially the same or at a steady state pressure gradient, then the pump will maintain substantially the same blood flow as there will be no substantial auto-regulation. If however, there are changes in the body pressure $P_{0b}$, resulting in a rise or fall in the inlet pressure $P_{1b}$, such that the change in pressure $\Delta P$ is either substantially higher or lower than the steady state pressure gradient, then the right pump 40b will compensate for this change in pressure by auto-regulating with an increase or a decrease in blood flow. An increase in the change in pressure $\Delta P$ over the steady state pressure gradient results in a decrease in blood flow while a decrease in the change in pressure $\Delta P$ relative to the steady state pressure gradient results in an increase in blood flow. The outflow generated is then pumped to the lungs and once oxygenated, pumped back to the heart.

As this blood flows back into the heart, it is transmitted through the left residual atrium 30a into the left manifold 120a from where it flows to the inlet the left pump 40a. Like the right pump 40b, the left pump 40a has an innate ability to respond to pressure differences between its inlet and its outlet. If there is an increase or a decrease in the inlet pressure $P_{1a}$, resulting from changes in the body pressure $P_{0a}$ as illustrated in FIG. 4, such that the change in pressure $\Delta P$ increases or decreases relative to the steady state pressure gradient, then the left pump will automatically compensate by auto-regulating with an increase or decrease in blood flow as described herein. The auto-regulated blood then flows to the rest of the body and back to the remnants of the right atrium 30b. This embodiment of the TAH system 100 therefore, involves a circulating system where blood is pumped through a mammalian cardiovascular system by a left 40a and right pump 40b that auto-regulate and asymmetrically balance for changes in pressure by either decreasing or increasing blood flow, with both pumps 40 acting individually to auto-regulate the changes on either the right or left side of the mammalian cardiovascular system and together to auto-regulate and asymmetrically balance the systemic pressure.

Figure 5:
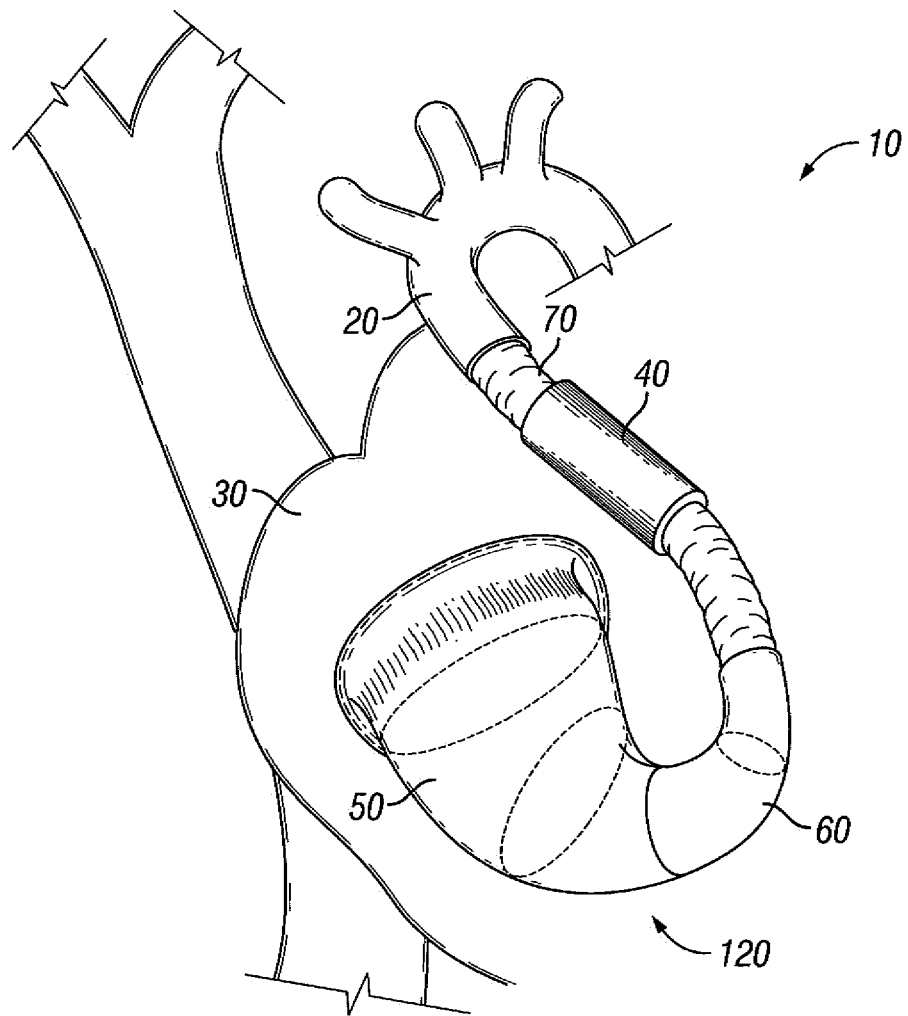
FIG. 5 illustrates a partial view of the TAH of FIG. 3 with the pumps attached further from the heart tissue on the ascending limbs of the U-shape formed by curved manifolds and short grafts extending from the pumps to the great vessels in accordance with an embodiment of the present invention.

FIG. 5, is an illustration of one part of the TAH system 100 showing the conical section 50 of the manifold sown unto the atrial remnant 30 at one end and the U-shaped section 60 of the manifold 120 snugly fitted at the other. The U-shaped section 60 then connects to the pump 40 at the opposite ascending limb of this U-shaped manifold with a short outflow graft 70 linking the pump 40 to a great vessel 20 at the other end of the pump 40. FIG. 5 also illustrates the laminar flow of blood from point A to point B allowing the pump 40 to have a direct and unobstructed view to pressure changes, thereby allowing the spinning elements in the pump 40 to detect the differences in inlet pressure and exploit this pressure sensitivity differences to automatically auto-regulate flow and asymmetrically balance the pressure in the mammalian cardiovascular system. The TAH system 100 includes two identical parts as outlined in FIG. 5, which operate in a dual synchronized manner by allowing each of the pumps 40 to immediately detect changes in the circulation system due to an acute reversible physiological stress event and automatically respond accordingly, by either increasing or decreasing of blood flow.

FIGS. 6a-6c are side views of the shape of a manifold 120 used in generating laminar flow and reducing pressure resistance and its component parts; the top conical section 50 and the lower U-shaped section 60. In FIG. 6a, the bottom of part the top conical section 50 is made to fit snugly into the top part of the lower U-shaped section 60 such that there is laminar flow and no stasis or shearing of the blood as it flows down the manifold 120 towards the pump 40. Though the top conical section 50 and the lower U-shaped section 60 are made to fit snugly, the lower U-shaped section 60 is still able to rotate about lower part of the top conical section 50 to ensure the best alignment during implantation of the TAH system 100. FIG. 6b is the top conical section 50 while FIG. 6c is the lower U-shaped section 60 and together they form the curved funnel shaped manifold 120 such that there is laminar flow and no stasis or shearing of the blood as it flows down the manifold 120 towards the pump 40.

Figure 7:
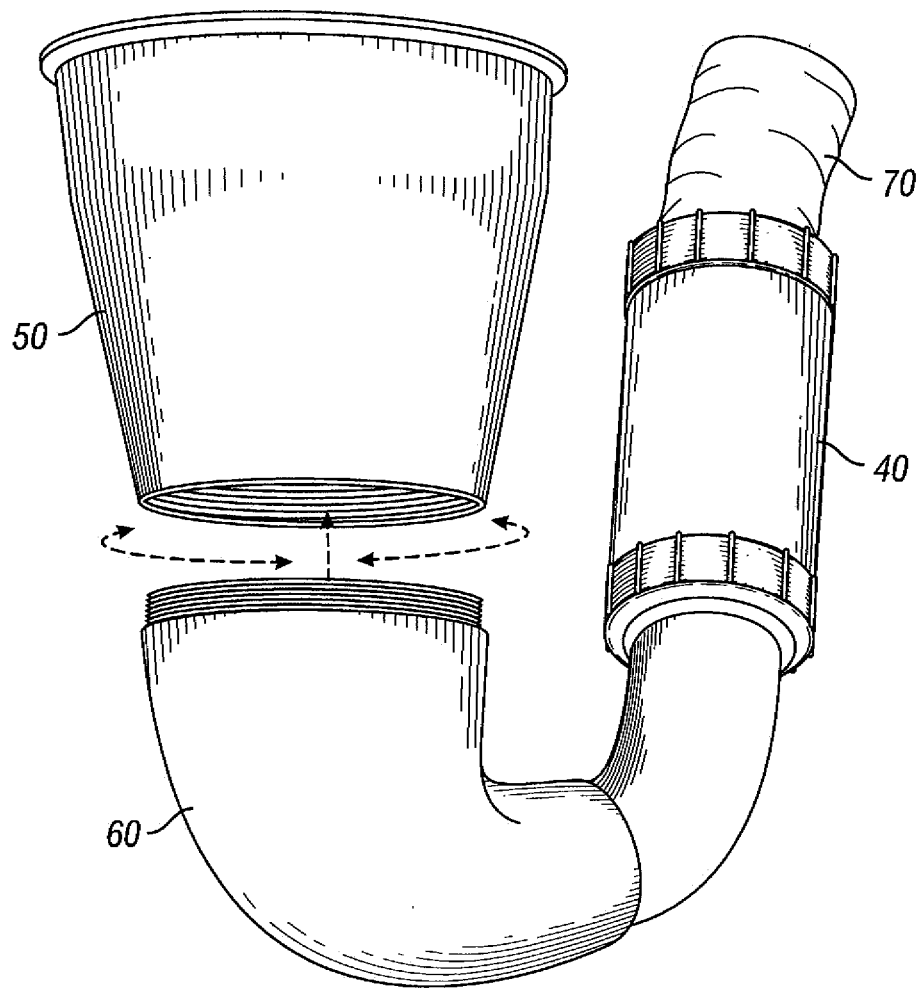
FIG. 7 illustrates upright view of the component parts of the manifold and the relationship of these components in generating laminar flow and minimizing intra-manifold pressure gradients that would attenuate the ability of the pump to respond to changes in atrial pressure in accordance with an embodiment of the present invention.

FIG. 7 illustrates an upright view of the manifold 120 and its component parts fitted together such that the lower U-shaped section 60 is still able to rotate around lower part of the top conical section 50 to ensure the best alignment during implantation of the TAH system 100. FIGS. 6a-6c also illustrate the combination of the manifold 120, the pump 40 and the outflow graft 70.

Figure 8A:
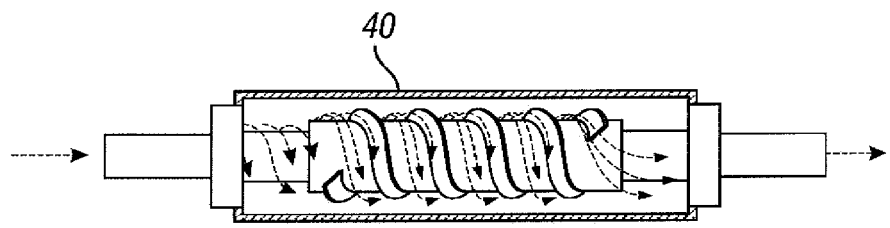
FIGS. 8a-8b illustrate different continuous flow pumps, one axial and the other centrifugal that can be used with an embodiment of the present invention.
Figure 8B:
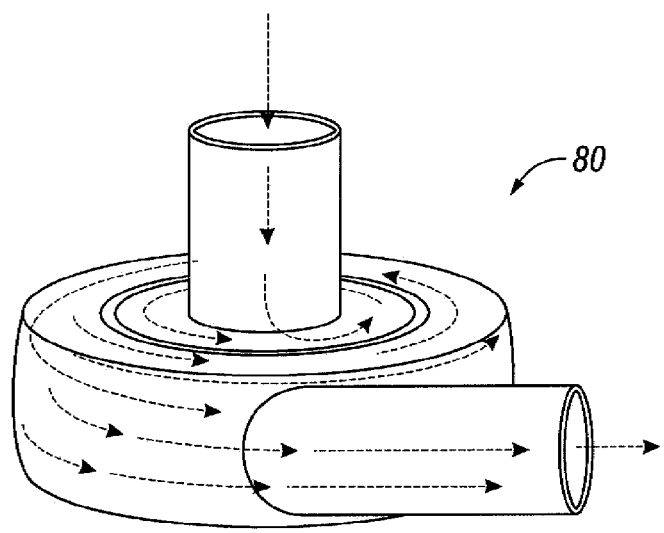

FIGS. 8a-8b illustrate different continuous flow pumps, one axial and the other centrifugal that can be used with an embodiment of the present invention. The axial pump like the centrifugal pump comprises of an inducer which prepares blood for spinning, the impeller which spins the blood and a straightener which passes the blood to the outflow graft 70. To understand the potential benefits of axial flow and centripetal flow pumps as they apply to TAH design, it may prove useful to contrast them with traditional volume displacement pumps.

Volume displacement pumps cyclically empty a passively filled chamber. Valves at the chamber inlet and outlet ensure that flow is unidirectional. When the chamber is allowed to expand, blood passively enters through the inlet valve; when the chamber is compressed, blood is ejected through the outlet valve. The flow or output produced by such devices is pulsed, spurting forward during the ejection phase and slowing or stopping during the filling phase, not unlike the output of the native heart. The mechanism of actuation varies, but generally involves an electromagnetic mechanism like a solenoid, (Novacor, WorldHeart), a low-speed high-torque motor coupled to a cam mechanism (HeartMate XVE, Thoratec), or external pneumatic actuation (HeartMate I, Thoratec pVAD). Although mechanistically simple, the large number of moving parts and the need for flexible membranes and valves significantly compromise durability. Prior to this report, all TAHs developed to date have utilized two such volume displacement pumps combined into a single device with one pump committed to the systemic circulation and one to the pulmonary.

Axial flow and centripetal flow pumps, in contrast, have a single rapidly spinning rotor or impeller that imparts hydraulic energy to the blood, resulting in continuous flow, like that produced by a water faucet. This mechanism obviates the need for valves or flexible membranes. Their mechanical simplicity makes these continuous flow pumps significantly smaller, more energy efficient, and much less susceptible to mechanical wear. These characteristics make them well suited for integration into a completely implantable TAH.

Although various embodiments of the TAH system have been illustrated in the accompanying Drawings and described in the foregoing Detailed Description, it will be understood that the invention is not limited to the embodiments disclosed, but is capable of numerous rearrangements, modifications, and substitutions without departing from the spirit of the invention as set forth herein.

We claim:

1. A total artificial heart system for a mammalian cardiovascular system comprising a right atrium, left atrium, aorta and pulmonary artery, the total artificial heart system comprising:

a first pump comprising a first pump inlet to receive a blood flow and a first pump outlet to pump the blood flow into the pulmonary artery and operable to selectively adjust the blood flow in response to a pressure differential between the first pump inlet and the first pump outlet;

a second pump comprising a second pump inlet to receive the blood flow and a second pump outlet to pump the blood flow into the aorta and operable to selectively adjust the blood flow in response to a pressure differential between the second pump inlet and the second pump outlet;

a first manifold comprising a first manifold inlet coupled to the right atrium and a first manifold outlet coupled to the first pump, wherein the first manifold transmits the blood flow such that a blood pressure of blood within the right atrium is substantially the same as a blood pressure of blood at the first pump inlet;

a second manifold comprising a second manifold inlet coupled to the left atrium and a second manifold outlet coupled to the second pump, wherein the second manifold transmits the blood flow such that a blood pressure of blood within the left atrium is substantially the same as a blood pressure of blood at the second pump inlet; and wherein the first pump and the second pump each comprise a centrifugal pump, and each pump is operable to change the blood flow rate through the pump in response to the pressure differential across the pump.

2. The total artificial heart system of claim 1, wherein the manifold is attached directly to the atrium of the subject.

3. The total artificial heart system of claim 1, wherein the manifold is a compliance chamber.

4. The total artificial heart system of claim 1, wherein the manifolds provide substantially no blood flow shear stress.

5. The total artificial heart system of claim 1, wherein the manifolds provide substantially no blood flow stasis.

6. The total artificial heart system of claim 1, wherein the manifolds are sized to accommodate a selected volume of blood such that the pumps can continue to auto-regulate blood flow rate in response to an increase in blood pressure due to an acute reversible physiological stress event.

7. The total artificial heart system of claim 1,
wherein the first manifold comprises a first nozzle to couple the first manifold to the to first pump, wherein the nozzle is adjustable to allow an adjustment in a positioning of the artificial heart system during a surgical procedure to couple the artificial heart system to the mammalian cardiovascular system.

8. The total artificial heart system of claim 1,
wherein the first pump pumps blood at a first output flow rate and the second pump pumps blood at a second output flow rate; and
wherein the first output flow rate and second output flow rate are maintained to substantially correspond to an asymmetric balance of blood flow rates between a right side and a left side of the mammalian cardiovascular system.

9. The total artificial heart system of claim 1, wherein the first manifold is shaped and configured into an unobstructive geometry to receive and direct blood flow such that a first blood flow pressure at the first manifold inlet is substantially the same as a second blood flow pressure at the first pump inlet.

10. The total artificial heart system of claim 1, wherein the second manifold is shaped and configured into an unobstructive geometry to receive and direct blood flow such that a third blood flow pressure at the second manifold inlet is substantially the same as a fourth blood flow pressure at the second pump inlet.

11. A total artificial heart system for a mammalian cardiovascular system comprising a right atrium, left atrium, aorta and pulmonary artery, the total artificial heart system comprising:

a first pump comprising a first pump inlet to receive a blood flow and a first pump outlet to pump the blood flow into the pulmonary artery and operable to selectively adjust the blood flow in response to a pressure differential between the first pump inlet and the first pump outlet;

a second pump comprising a second pump inlet to receive the blood flow and a second pump outlet to pump the blood flow into the aorta and operable to selectively adjust the blood flow in response to a pressure differential between the second pump inlet and the second pump outlet;

a first manifold comprising a first manifold inlet coupled to the right atrium and a first manifold outlet coupled to the first pump, wherein the first manifold transmits the blood flow such that a blood pressure of blood within the right atrium is substantially the same as a blood pressure of blood at the first pump inlet;

a second manifold comprising a second manifold inlet coupled to the left atrium and a second manifold outlet coupled to the second pump, wherein the second manifold transmits the blood flow such that a blood pressure of blood within the left atrium is substantially the same as a blood pressure of blood at the second pump inlet; and wherein one pump is an axial continuous flow pump and the other is a continuous flow centrifugal pump, and each pump is operable to change the blood flow rate through the pump in response to the pressure differential across the pump.

12. The total artificial heart system of claim 11, wherein the manifold is attached directly to the atrium of the subject.

13. The total artificial heart system of claim 11, wherein the manifold is a compliance chamber.

14. The total artificial heart system of claim 11, wherein the manifolds provide substantially no blood flow shear stress.

15. The total artificial heart system of claim 1, wherein the manifolds provide substantially no blood flow stasis.

16. The total artificial heart system of claim 1, wherein the manifolds are sized to accommodate a selected volume of blood such that the pumps can continue to auto-regulate blood flow rate in response to an increase in blood pressure due to an acute reversible physiological stress event.

17. The total artificial heart system of claim 1,
wherein the first manifold comprises a first nozzle to couple the first manifold to the to first pump, wherein the nozzle is adjustable to allow an adjustment in a positioning of the artificial heart system during a surgical procedure to couple the artificial heart system to the mammalian cardiovascular system.

18. The total artificial heart system of claim 1,
wherein the first pump pumps blood at a first output flow rate and the second pump pumps blood at a second output flow rate; and
wherein the first output flow rate and second output flow rate are maintained to substantially correspond to an asymmetric balance of blood flow rates between a right side and a left side of the mammalian cardiovascular system.

19. The total artificial heart system of claim 11, wherein the first manifold is shaped and configured into an unobstructive geometry to receive and direct blood flow such that a first blood flow pressure at the first manifold inlet is substantially the same as a second blood flow pressure at the first pump inlet.

20. The total artificial heart system of claim 11, wherein the second manifold is shaped and configured into an unobstructive geometry to receive and direct blood flow such that a third blood flow pressure at the second manifold inlet is substantially the same as a fourth blood flow pressure at the second pump inlet.

\* \* \* \* \*